US009301701B2

(12) United States Patent
McEwen et al.

(10) Patent No.: US 9,301,701 B2
(45) Date of Patent: Apr. 5, 2016

(54) METHOD FOR MEASURING TOURNIQUET LIMB OCCLUSION PRESSURE

(71) Applicant: Western Clinical Engineering, Ltd., Vancouver (CA)

(72) Inventors: James A. McEwen, Vancouver (CA); Michael Jameson, North Vancouver (CA); William K. W. Cheung, Vancouver (CA); Michael A. Gebert, Vancouver (CA)

(73) Assignee: Western Clinical Engineering Ltd., Vancouver (CA)

( * ) Notice: Subject to any disclaimer, the term of this patent is extended or adjusted under 35 U.S.C. 154(b) by 280 days.

(21) Appl. No.: 13/847,999

(22) Filed: Mar. 20, 2013

(65) Prior Publication Data
US 2013/0226013 A1 Aug. 29, 2013

Related U.S. Application Data

(62) Division of application No. 11/938,043, filed on Nov. 9, 2007, now Pat. No. 8,425,426.

(51) Int. Cl.
*A61B 5/02* (2006.01)
*A61B 5/0225* (2006.01)
(Continued)

(52) U.S. Cl.
CPC ........... *A61B 5/02255* (2013.01); *A61B 5/0235* (2013.01); *A61B 5/0261* (2013.01);
(Continued)

(58) Field of Classification Search
None
See application file for complete search history.

(56) References Cited

U.S. PATENT DOCUMENTS 3,239,257 A 3/1966 White
4,321,929 A 3/1982 Lemelson
(Continued)

FOREIGN PATENT DOCUMENTS

CA 2198482 3/1996
CA 200981 11/1999
(Continued)

OTHER PUBLICATIONS

AORN Standards, Recommended Practices, and Guidelines, 2007 Edition; Recommended Practices for the Use of the Pneumatic Tourniquet in the Perioperative Practice Setting; circa Jan. 1, 2007; pp. 617-629.
(Continued)

*Primary Examiner* — Navin Natnithithadha
*Assistant Examiner* — Michael R Bloch
(74) *Attorney, Agent, or Firm* — Klarquist Sparkman, LLP

(57) ABSTRACT

Improved tourniquet apparatus for measuring a patient's limb occlusion pressure includes an inflatable tourniquet cuff for encircling a limb at a location and to which a tourniquet instrument is releasably connectable. The instrument includes pressure sensing for producing a cuff pressure signal indicative of the level of pressure in the cuff, a pressure regulation mechanism communicating with the cuff and responsive to the cuff pressure signal for moving fluid into and out of the cuff, thereby regulating the pressure in the cuff, a blood flow transducer for producing a blood flow signal indicative of blood flow past the cuff, and limb occlusion pressure means responsive to the blood flow signal and the cuff pressure signal for increasing the cuff pressure level until blood flow indicated by the blood flow signal decreases to a level less than a minimum detection threshold, and then suspending fluid movement into and out of the cuff to produce a limb occlusion pressure value that is indicative of a pressure in the cuff when the fluid motion is suspended.

11 Claims, 6 Drawing Sheets

(51) Int. Cl.
*A61B 17/135* (2006.01)
*A61B 5/022* (2006.01)
*A61B 5/0235* (2006.01)
*A61B 5/026* (2006.01)
*A61B 5/00* (2006.01)

(52) U.S. Cl.
CPC ............. *A61B5/02233* (2013.01); *A61B 5/746* (2013.01); *A61B 17/135* (2013.01); *A61B 17/1355* (2013.01)

(56) References Cited

U.S. PATENT DOCUMENTS

| | | |
|---|---|---|
| 4,469,099 A | 9/1984 | McEwen |
| 4,479,494 A | 10/1984 | McEwen |
| 4,520,819 A | 6/1985 | Birmingham |
| 4,520,820 A | 6/1985 | Kitchin |
| 4,548,198 A | 10/1985 | Manes |
| 4,605,010 A | 8/1986 | McEwen |
| 4,635,635 A | 1/1987 | Robinette-Lehman |
| 4,671,290 A | 6/1987 | Miller |
| 4,869,265 A | 9/1989 | McEwen |
| 5,048,536 A | 9/1991 | McEwen |
| 5,181,522 A | 1/1993 | McEwen |
| 5,254,087 A | 10/1993 | McEwen |
| 5,312,431 A | 5/1994 | McEwen |
| 5,439,477 A | 8/1995 | McEwen |
| 5,454,831 A | 10/1995 | McEwen |
| 5,556,415 A | 9/1996 | McEwen |
| 5,569,304 A | 10/1996 | Ulrich |
| 5,578,055 A | 11/1996 | McEwen |
| 5,584,853 A | 12/1996 | McEwen |
| 5,607,447 A | 3/1997 | McEwen |
| 5,649,954 A | 7/1997 | McEwen |
| 5,681,339 A | 10/1997 | McEwen |
| 5,741,295 A | 4/1998 | McEwen |
| 5,842,996 A | 12/1998 | Gruenfeld |
| 5,846,190 A * | 12/1998 | Woehrle ........................ 600/330 |
| 5,855,589 A * | 1/1999 | McEwen et al. ............. 606/202 |
| 5,911,735 A | 6/1999 | McEwen |
| 5,935,146 A | 8/1999 | McEwen |
| 5,951,502 A | 9/1999 | Peeler |
| 6,050,951 A | 4/2000 | Friedman |
| 6,051,016 A | 4/2000 | Mesaros |
| 6,213,939 B1 | 4/2001 | McEwen |
| 6,371,937 B1 | 4/2002 | McPhee |
| 6,475,228 B1 | 11/2002 | Mesaros |
| 6,589,268 B1 | 7/2003 | McEwen |
| 6,605,103 B2 | 8/2003 | Hovanes |
| 6,682,547 B2 | 1/2004 | McEwen |
| 7,331,977 B2 | 2/2008 | McEwen |
| 7,479,154 B2 | 1/2009 | McEwen |
| 2003/0036771 A1 | 2/2003 | McEwen |
| 2003/0126912 A1 | 7/2003 | Cook |
| 2003/0167070 A1 | 9/2003 | McEwen |
| 2003/0236548 A1 | 12/2003 | Hovanes |
| 2004/0147956 A1 | 7/2004 | Hovanes |
| 2006/0224181 A1 | 10/2006 | McEwen |
| 2006/0253150 A1 * | 11/2006 | McEwen et al. ............. 606/202 |
| 2006/0287672 A1 | 12/2006 | McEwen |
| 2007/0032818 A1 | 2/2007 | McEwen |
| 2007/0032819 A1 | 2/2007 | McEwen |
| 2007/0167844 A1 | 7/2007 | Asada |
| 2007/0255310 A1 | 11/2007 | Hovanes |
| 2008/0262533 A1 | 10/2008 | McEwen |
| 2009/0112104 A1 | 4/2009 | Usuda et al. |
| 2009/0124912 A1 | 5/2009 | McEwen |
| 2010/0211096 A1 | 8/2010 | McEwen |

FOREIGN PATENT DOCUMENTS

| | | |
|---|---|---|
| CA | 2607134 | 11/2006 |
| JP | 63-317131 | 12/1988 |
| JP | 2001299707 | 10/2001 |
| WO | 8300995 | 3/1983 |
| WO | 9606568 | 3/1996 |
| WO | 0197747 | 12/2001 |
| WO | 2006116837 | 11/2006 |
| WO | 2007064654 | 7/2007 |

OTHER PUBLICATIONS

International Search Report and Written Opinion: related application No. PCT/CA2008/001923; Feb. 13, 2009; 6 pages.

Office action, English; Japan Patent Office; related application 2010-532387; Jun. 3, 2014; 2 pages.

* cited by examiner

METHOD FOR MEASURING TOURNIQUET LIMB OCCLUSION PRESSURE

FIELD OF THE INVENTION

This invention pertains to pneumatic tourniquet systems commonly used for stopping the flow of arterial blood into a portion of a surgical patient's limb to facilitate the performance of a surgical procedure, and for facilitating intravenous regional anesthesia. In particular, this invention pertains to pneumatic tourniquet apparatus for measuring the minimum pressure that must be applied to stop arterial blood flow into the portion of the limb to facilitate surgery.

BACKGROUND OF THE INVENTION

Surgical tourniquet systems are commonly used to stop the flow of arterial blood into a portion of a patient's limb, thus creating a clear, dry surgical field that facilitates the performance of a surgical procedure and improves outcomes. A typical surgical tourniquet system of the prior art includes a tourniquet cuff for encircling a patient's limb at a desired location, a tourniquet instrument, and flexible tubing connecting the cuff to the instrument. In some surgical tourniquet systems of the prior art, the tourniquet cuff includes an inflatable portion, and the inflatable portion of the cuff is connected pneumatically through one or two cuff ports by flexible plastic tubing to a tourniquet instrument that includes a pressure regulator to maintain the pressure in the inflatable portion of the cuff, when applied to a patient's limb at a desired location, near a reference pressure that is above a minimum pressure required to stop arterial blood flow past the cuff during a time period suitably long for the performance of a surgical procedure. Many types of such pneumatic surgical tourniquet systems have been described in the prior art, such as those described by McEwen in U.S. Pat. No. 4,469,099, U.S. Pat. No. 4,479,494, U.S. Pat. No. 5,439,477 and by McEwen and Jameson in U.S. Pat. No. 5,556,415 and U.S. Pat. No. 5,855,589.

Some advanced tourniquet systems include tourniquet cuffs that have two separate pneumatic cuff ports, so that two separate pneumatic passageways can be established between the inflatable portion of the cuff and the tourniquet instrument, by separately connecting flexible plastic tubing between each port and the instrument. Such systems are often called dual-port tourniquet systems. In one such dual-port tourniquet system of the prior art, described in U.S. Pat. No. 4,469,099, the pneumatic pressure regulation elements within the tourniquet instrument communicate pneumatically with the inflatable portion of the cuff through one port, and a pressure sensor within the tourniquet instrument communicates pneumatically with the inflatable portion of the cuff through the second port. This configuration enables more accurate sensing, monitoring and continuous regulation of the actual pressure in the inflatable portion of the cuff that encircles the patient's limb, in comparison to single-port tourniquet systems.

In a typical single-port tourniquet system of the prior art, the tourniquet cuff has only one port and only one pneumatic passageway is established between the tourniquet cuff and the instrument. The actual cuff pressure must be sensed indirectly, through the same tubing and port that is used to increase, decrease and regulate the pressure in the cuff during surgery. As a result, in such a single-port tourniquet system of the prior art, the accuracy and speed of pressure regulation, and the accuracy of the sensed cuff pressure, are affected by the pneumatic flow resistance within the single port and within the flexible plastic tubing that pneumatically connects the port and cuff to the tourniquet instrument. These characteristics inherent in single-port tourniquet systems may also affect the accuracy and speed of measurement of Limb Occlusion Pressure (LOP, defined below), in comparison to dual-port tourniquet systems.

Many studies published in the medical literature have shown that the safest tourniquet pressure is the lowest pressure that will stop the flow of arterial blood past a specific cuff applied to a specific patient for the duration of that patient's surgery. Such studies have shown that higher tourniquet pressures are associated with higher risks of tourniquet-related injuries to the patient. Therefore, when a tourniquet is used in surgery, surgical staff generally try to use the lowest tourniquet pressure that in their judgment is safely possible.

It is well established in the medical literature that the optimal guideline for setting the pressure of a constant-pressure tourniquet is based on Limb Occlusion Pressure (LOP). LOP can be defined as the minimum pressure required, at a specific time in a specific tourniquet cuff applied to a specific patient's limb at a specific location, to stop the flow of arterial blood into the limb distal to the cuff. The currently established guideline for setting tourniquet pressure based on LOP is that an additional safety margin of pressure is added to the measured LOP, to account for physiologic variations and other changes that may be anticipated to occur normally over the duration of a surgical procedure.

Surgical staff can measure LOP manually by detecting the presence of arterial pulsations in the limb distal to a tourniquet cuff as an indicator of arterial blood flow past the cuff and into the distal limb. Such arterial pulsations can be defined as the rhythmical dilation or throbbing of arteries in the limb distal to the cuff due to blood flow produced by regular contractions of the heart. Detecting blood flow thus can be done using palpation, Doppler ultrasound or photoplethysmography to measure arterial pulsations. One technique for manual measurement of LOP based on monitoring arterial pulsations as an indicator of arterial blood flow is as follows: tourniquet cuff pressure is increased by an operator slowly from zero while monitoring arterial pulsations in the limb distal to the cuff until the pulsations can no longer be detected; the lowest tourniquet cuff pressure at which the pulsations can no longer be detected can be defined as the ascending LOP. A second manual technique is that an operator can slowly decrease tourniquet cuff pressure while monitoring to detect the appearance of arterial pulsations distal to the cuff; the highest pressure at which arterial pulsations are detected can be defined as the descending LOP. The accuracy of such manual measurements of LOP is very dependent on the sensitivity, precision and noise immunity of the technique for detecting and monitoring arterial pulsations, and on operator skill, technique and consistency. Under the best circumstances considerable elapsed time is required on the part of a skilled, experienced and consistent operator, using a sensitive and precise technique for detecting and monitoring pulsations as an indicator of distal blood flow, to accurately measure LOP by manual means.

Some surgical tourniquet systems of the prior art include means to measure LOP automatically. Prior-art tourniquet apparatus having automatic LOP measurement means are described by McEwen in U.S. Pat. No. 5,439,477, by McEwen and Jameson in U.S. Pat. No. 5,556,415 and by McEwen et al in co-pending US Patent Application Publication No. 20060253150. Such prior-art systems have included blood flow transducers that employ a photoplethysmographic principle to sense blood flow in the distal limb, although other transducers have been suggested in the prior art to measure blood flow based on other principles. A blood flow transducer employing the photoplethysmographic principle uses light to indicate the volume of blood present in a transduced region, consisting of a combination of a residual blood volume and a changing blood volume resulting from arterial pulsations. An additional pressure margin based on recommendations in published surgical literature is added to the automatically measured LOP to provide a "Recommended Tourniquet Pressure" (RTP), as a guideline to help the surgical staff select the lowest tourniquet pressure that will safely stop arterial blood flow for the duration of a surgical procedure. Such prior-art systems allow the surgical staff to select the RTP, based on LOP, as the tourniquet pressure for that patient or to select another pressure based on the physician's discretion or the protocol at the institution where the surgery is being performed. The difference in pressure between the measured LOP and the tourniquet pressure selected for surgery, which may be the RTP, can be defined as the cuff pressure safety margin. Ideally the cuff pressure safety margin is selected to be greater than the magnitude of any increase in LOP normally expected during surgery due to changes caused by drugs used for anesthesia, the patient's physiologic response to surgery and other variables. Change in blood pressure is one physiologic characteristic that varies during surgery and has been shown to affect the LOP during surgery, and therefore the cuff pressure safety margin during surgery. For example, an increase in the patient's blood pressure will lead to an increase in LOP, with attendant decrease in the safety margin.

Despite their potential to recommend near-optimal settings of surgical tourniquet pressures for individual patients, some prior-art surgical tourniquet systems that include means for automatic measurement of LOP have demonstrated limitations of performance that have prevented their widespread acceptance and routine use. The limitations are primarily in four areas: safety, probability of successful LOP measurement, speed of LOP measurement, and accuracy of LOP measurement.

Regarding safety, it is desirable during LOP measurement that the tourniquet cuff pressure not rise significantly above the pressure required to stop blood flow past the cuff for a significant period of time. This is because it is well established that the possibility of tourniquet-related injuries increases if tourniquet cuff pressure increases substantially. For this reason, prior-art tourniquet apparatus that measures LOP by descending from a high cuff pressure are considered to be less desirable than tourniquet apparatus that measures LOP by ascending from a low pressure. Also regarding safety, it is desirable that LOP measurements be made as quickly as possible, while still assuring that the resulting LOP measurement is sufficiently accurate to allow setting the tourniquet pressure based on the measured LOP. Speed of LOP measurement is desirable for three reasons related to safety and performance: first, it is well established that longer tourniquet times are associated with a higher possibility of tourniquet-related injuries; second, during LOP measurement, if venous outflow of blood from the limb is restricted by a pressurized tourniquet cuff for an excessively long period of time, then pooling of blood in the distal limb from arterial inflow may occur, possibly leading to passive congestion of the limb from residual blood that may be hazardous; and third, any continuing increase of residual blood in the distal limb over an extended measurement period may lead to measurement error in photoplethysmographic blood flow transducers, because such transducers inherently provide one indication of the combination of residual blood volume and varying blood volume resulting from arterial pulsations in the transduced portion, thus lengthening the time for successful completion of LOP measurement, or making successful LOP measurement impossible.

Experience with manual LOP measurement, and with prior-art tourniquet apparatus having LOP measurement capability, has shown that it is not possible in practice to measure the LOP of all patients. This is because the quality and magnitude of arterial blood flow measured by a blood flow transducer distal to the tourniquet cuff may not be sufficient in some patients for measurement or analysis, due to a variety of anatomic and physiologic factors. For such patients, the physician must revert to a standard tourniquet pressure setting based on the physician's discretion. Co-pending US Patent Application Publication No. 20060253150 describes means for characterizing some aspects of the quality of blood flow distal to the tourniquet cuff measured by a blood flow transducer, in order to quickly identify some patients and situations in which LOP measurement is unlikely to be successfully completed. No tourniquet system known in the prior art provides a blood flow transducer having an indication of the quality of blood flow at the transducer that is perceptible to an operator, to assist the operator in positioning and adjusting the blood flow transducer on the limb to improve the quality of measured blood flow prior to initiation of LOP measurement.

Even for patients in whom LOP measurement is possible, the time required by some tourniquet systems known in the prior art to successfully complete automatic LOP measurements may be considerable. In addition to the safety-related considerations described above, the extended time required for LOP measurement by some prior-art tourniquet systems may significantly disrupt or delay normal activities in the operating room, and thus affect the efficiency of surgery. This is in part because the patient's operative limb must remain motionless during the measurement period, to avoid the introduction of variations in pneumatic cuff pressure and the introduction of noise due to movement of the distal blood flow transducer relative to the limb. In some prior-art apparatus for measuring LOP, the reference pressure for the tourniquet cuff is typically increased from zero in many predetermined increments of increasing pressure. After each such predetermined increment or step of the reference pressure, time is required to allow the actual increased pressure within the tourniquet cuff to stabilize before measurements can be taken from the distal blood flow transducer and related to actual cuff pressure. For single-port tourniquet systems of the prior art, the time required for the cuff pressure to stabilize is significant. Substantially increasing the predetermined step size in such prior-art systems might increase the speed of LOP determination, but could also decrease the accuracy of LOP measurement significantly. Thus the total time required for sufficiently accurate LOP measurement in these prior-art systems can be substantial, and includes the time required to increase the reference pressure in many predetermined steps from zero, the time required to allow the actual cuff pressure to stabilize after each step, and the time required to take a measurement from the distal blood flow transducer at each step, until LOP measurement is successfully completed or until an arbitrary maximum pressure limit is reached without LOP being measured.

The accuracy of LOP measurements by prior-art tourniquet apparatus may be affected by three additional sources of error. First, because of the substantial time periods often required to measure LOP by prior-art tourniquet apparatus, error may be introduced into the LOP measurement due to accumulation of residual blood in the limb distal to the tourniquet cuff. This gradual accumulation of residual blood due to blocking of venous outflow by the tourniquet cuff can reduce the magnitude of the pulsations in blood volume that are associated with the rhythmical dilation or throbbing of the distal arteries over the duration of each cardiac cycle, from heartbeat to heartbeat. Also, such an increasing volume of residual blood in the distal limb during a measurement interval can cause a gradual change in the mean blood flow signal from a photoplethysmographic transducer during the period, for reasons described above. Such a gradual change may make valid arterial pulsations indicating arterial blood flow difficult or impossible to detect, and reduces the maximum possible amplification of the signal from the distal blood flow transducer, thus reducing the accuracy of subsequent analysis. A second source of error in LOP measurement by some prior-art tourniquet apparatus results from movement of the patient's limb and movement of the distal blood flow transducer relative to the attached limb, either of which could mask valid arterial pulsations indicating blood flow or could be misinterpreted as valid arterial pulsations. A third source of error in LOP measurement by prior-art tourniquet apparatus results from improper application and use of the photoplethysmographic transducer. For example, the transducer may be not be applied properly to the digit of a limb by the operator, or the transducer may be applied so that it is exposed to the direct illumination of surgical lighting.

There is a need for improved surgical tourniquet apparatus for measuring LOP, to overcome the above-described limitations of prior-art tourniquet systems, so that such apparatus will be suitable for routine use in all surgical procedures. To be routinely useful in this context, apparatus for measuring LOP automatically should not introduce secondary hazards associated with the measurement of LOP, should indicate to an operator whether an LOP measurement is possible prior to initiation, should have a high probability of successful completion after LOP measurement is initiated, should complete LOP measurement sufficiently fast so that the measurement of LOP does not disrupt or unduly delay normal activities in the operating room, should result in an LOP measurement that is accurate within surgically acceptable expectations so that it can be used as the basis for optimal setting of tourniquet pressure. Also, after initial setting of tourniquet pressure, it would be desirable to provide an operator with an ongoing indication of the tourniquet cuff pressure safety margin during surgery. Certain improvements to tourniquet apparatus for measuring LOP have been described in co-pending US Patent Application No. 20060253150. The present invention further addresses the need for improved tourniquet apparatus for measuring LOP.

DETAILED DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Hardware

Figure 1:
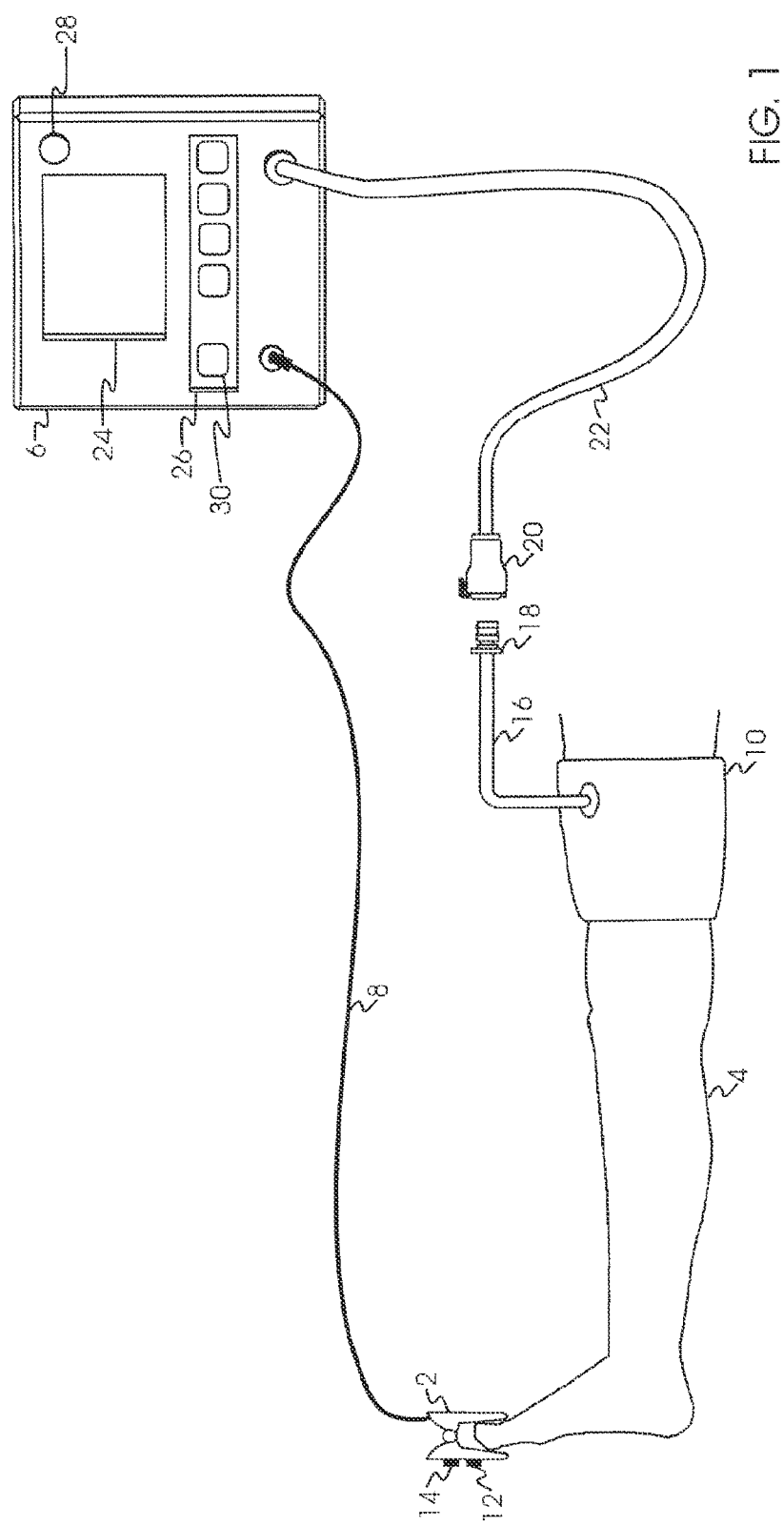
FIG. 1 is a pictorial representation of the preferred embodiment in a surgical application.

FIG. 1 shows blood flow transducer 2 applied to a digit of patient limb 4 and connected to instrument 6 via multi-conductor shielded cable 8. Blood flow transducer 2 is positioned on patient limb 4 at a location that is distal to pressurizing cuff 10 which is also shown applied to patient limb 4. This configuration permits blood flow transducer 2 to detect blood flow in patient limb 4 and changes in blood flow that occur in patient limb 4 as a result of the pressurization of cuff 10. Blood flow transducer 2 is used by instrument 6 when instrument 6 is performing automatic measurements of limb occlusion pressure (LOP). LOP has been defined above to be the minimum pressure required, at a specific time in a specific tourniquet cuff applied to a specific patient's limb at a specific location, to stop the flow of arterial blood into the limb distal to the cuff.

Blood flow signal quality indicator 12 forms part of blood flow transducer 2 and is configured such that it is readily visible to an operator of transducer 2. In the preferred embodiment blood flow signal quality indicator 12 is a bi-color green and red LED, but it will be apparent that other types of indicators visible to the operator of transducer 2 could be employed. The green LED of blood flow signal quality indicator 12 is illuminated to provide an indication of when signals representative of blood flow detected by transducer 2 exceed predetermined minimum quality criteria and an automatic measurement of limb occlusion pressure may proceed. If the signals representative of blood flow detected by transducer 2 do not exceed predetermined minimum quality criteria, the red LED of blood flow signal quality indicator 12 is illuminated and the automatic measurement of limb occlusion pressure is inhibited until the operator repositions the transducer or makes other adjustments to improve signal quality. The immediate feedback of blood flow signal quality at the location of blood flow transducer 2 provides the operator with a convenient means to be assured that blood flow transducer 2 has been correctly applied to a digit of a patient limb 4, a blood flow signal of acceptable quality is available, and that an automatic measurement of LOP is possible.

Blood flow transducer 2 also includes LOP measurement key 14, which when depressed will initiate the automatic measurement of limb occlusion pressure.

Cuff 10 is pneumatically connectable to instrument 6. The inflatable portion of pressurizing cuff 10 has one pneumatic connection and is generally similar in design and construction to the cuffs described by McEwen in U.S. Pat. No. 5,741,295, U.S. Pat. No. 5,649,954, U.S. Pat. No. 5,484,831 and by Robinette-Lehman in U.S. Pat. No. 4,635,635. Cuff 10 is adapted for use in a sterile surgical field in an operating room environment by being formed of materials that can withstand, and that can be sterilized by, techniques normally used to sterilize medical devices to a level of sterility that allows them to be safely used within a sterile surgical field. Cuff 10 is a single-port cuff, a pneumatic passageway to the inflatable portion of cuff 10 is provided by cuff port 16. In FIG. 1 cuff port 16 of sufficient length to allow a pneumatic connection to cuff 10 to be made outside of a sterile surgical field. Cuff port 16 is fitted with male locking connector 18 (DSM2202, Colder Products Company, St. Paul, Minn.), and mate to form releasable pneumatic connection with female locking connector 20 (PMC1704, Colder Products Company, St. Paul, Minn.). For clarity, the connectors illustrated in FIG. 1 are shown disconnected; in the following description of the preferred embodiment the connectors are mated and form part of the pneumatic passageway between instrument 6 and cuff 10. The pneumatic connection from instrument 6 to cuff 10 is made by flexible plastic tubing 22 which is fitted with female locking connector 20.

As can be seen in FIG. 1, instrument 6 includes an operator interface consisting of graphic display panel 24, keypad 26, and visual alarm indicator 28. Display panel 24 is employed for the selective display of any of the following alphanumeric information: limb occlusion pressures, recommended tourniquet pressures and cuff pressure safety margins as measured and updated by instrument 6; actual cuff pressures as measured by instrument 6; reference or "set" cuff pressure levels, alarm reference "limits" or values; alphanumeric alarm messages describing detected alarm conditions and other information required for the operation of instrument 6.

Keypad 26 provides a means for an operator of instrument 6 to control the operation of instrument 6. Keypad 26 includes a limb occlusion pressure measurement (LOP) key 30, which when depressed will initiate the measurement of LOP as described further below. Keypad 26 also has an "inflate" key to initiate the inflation of cuff 10, a "deflate" key to initiate the deflation of cuff 10, and other keys to permit the operator of instrument 6 to adjust the reference pressure level and set inflation time and other alarm limits.

Visual alarm indicator 28 is a bright red light emitting diode (LED) which is activated by instrument 6 in response to detected alarm conditions. Instrument 6 also signals the presence of an alarm condition by generating an audible tone to further alert the operator to the presence of an alarm condition and displays alarm text messages describing the alarm condition on display panel 24. One example of a detected alarm condition that requires the operator's attention is a change in the cuff pressure safety margin as described elsewhere below.

Figure 2:
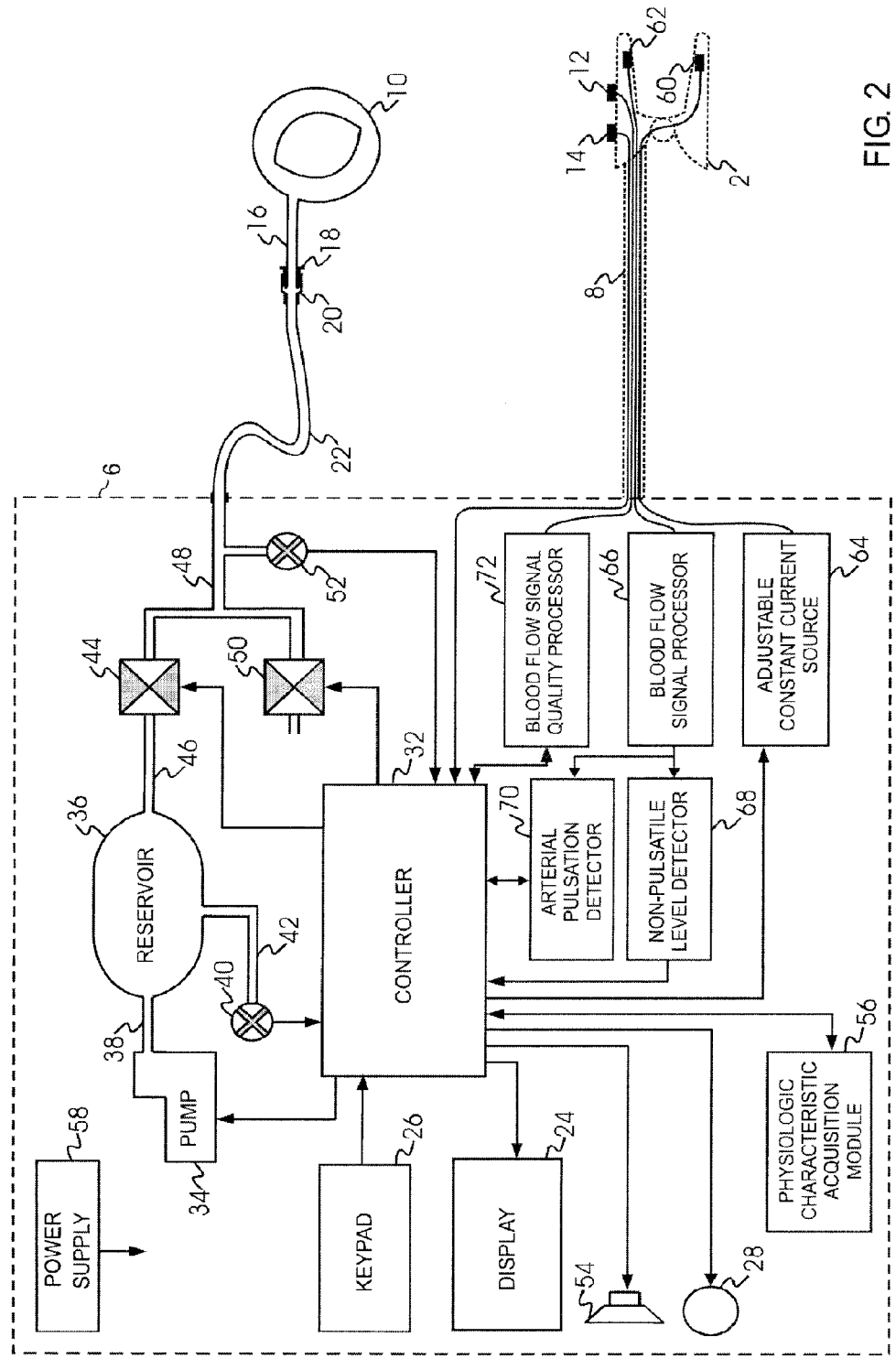
FIG. 2 is a block diagram of the preferred embodiment.

Referring to the block diagram of instrument 6 shown in FIG. 2, controller 32 comprises a microcontroller (MC68HC16Z1, Freescale Semiconductor, Austin, Tex.), associated memory and control software, analog and digital peripheral interface circuitry, and other necessary support components.

As shown in FIG. 2, pneumatic pump 34 (KNF Neuberger, Inc., Trenton, N.J.) is pneumatically connected to reservoir 36 by tubing 38. In response to control signals from controller 32, pump 34 operates to pressurize reservoir 36. Reservoir pressure transducer 40 is pneumatically connected by tubing 42 to reservoir 36 and generates a reservoir pressure signal. The reservoir pressure signal is communicated to controller 32. Controller 32 acts to maintain the pressure in reservoir 36 near a reservoir pressure level. Controller 32 sets the reservoir pressure level to a pressure above the reference pressure level set by the operator of instrument 6 or automatically by controller 32 during a limb occlusion pressure measurement; the reservoir pressure level is set to a level significantly greater than the reference pressure level, typically 100 mmHg Controller 32 in response to the reservoir pressure level and the reservoir pressure signal activates pump 34 to maintain the level of the reservoir pressure signal near the reservoir pressure level.

Inflation valve 44 (EVO-3-12V, Clippard Instrument Laboratory, Cincinnati, Ohio) is configured as a two position normally closed valve. One side of the valve is pneumatically connected via tubing 46 to reservoir 36 the other side of the valve is connected to cuff 10 via the pneumatic passageway formed by manifold 48, tubing 22, connectors 20 and 18 and cuff port 16. When energized by controller 32, inflation valve 44 moves to the open position and allows pressurized gas to flow from reservoir 36 to cuff 10, thereby increasing the pressure of gas in the inflatable portion of cuff 10.

Deflation valve 50 (EVO-3-12V, Clippard Instrument Laboratory, Cincinnati, Ohio) is configured as a two position normally closed valve. One side of the valve is pneumatically connected to cuff 10 via the pneumatic passageway formed by manifold 48, tubing 22, connectors 20 and 18 and cuff port 16, the other side is open to atmosphere. When energized by controller 32, deflation valve 50 moves to the open position and allows pressurized gas to flow from cuff 10 to atmosphere, thereby decreasing the pressure of gas in the inflatable portion of cuff 10.

Cuff pressure transducer 52 is pneumatically connected to cuff 10 via manifold 48 and the pneumatic passageway formed by tubing 22, connectors 20 and 18 and cuff port 16 and generates a cuff pressure signal which is communicated to controller 32. Controller 32 is able to resolve changes in the cuff pressure signal as small as 0.15 mmHg. An accurate measurement of the actual pressure of gas within cuff 10 by cuff pressure transducer 52 is possible when deflation valve 50 and inflation valve 44 are both closed because there is no gas flow in the pneumatic passageways connecting transducer 52 to the inflatable portion of cuff 10. To enable accurate cuff pressure measurements during the measurement of Limb Occlusion Pressure, deflation valve 50 and inflation valve 44 are both temporarily closed at selected times, thereby suspending pressure regulation during those times as described further below. As noted above, controller 32 will, in response to generated alarm signals alert the operator of an alarm condition by activating visual alarm indicator 28 and producing audible tones. Speaker 54 is connected to controller 32, and electrical signals having different frequencies to specify different alarm signals and conditions are produced by controller 32 and converted to audible sound by loudspeaker 54.

During surgery a patient's physiologic status is monitored by means of a patient monitor. Physiologic characteristics that are typically monitored include blood pressure values resulting from periodic non-invasive or continuous blood pressure measurements, heart rate values, temperature values, oxygen saturation and other parameters. As shown in FIG. 2 instrument 6 includes a physiologic characteristic acquisition module 56 for communication with an external patient monitor. Physiologic characteristic acquisition module 56 is electronic circuitry and software that is configured for communicating with the data communication interface of an external patient monitor to acquire the values of monitored physiologic characteristics such as blood pressure. As described further below, to allow an updated cuff pressure safety margin to be computed and displayed, controller 32 via physiologic characteristic acquisition module 56 requests and receives the current values of the patient's blood pressure near the time of LOP measurement and subsequently while cuff 10 is pressurized to occlude blood flow.

Power supply 58 connects to an external AC supply and provides regulated DC power for the normal operation of all electronic components of instrument 6. Power supply 58 may also include a battery to enable instrument 6 to continue to operate in the absence of an external AC supply.

Pressure Regulation

An operator of instrument 6 may use keypad 26 to select a reference pressure level; this is the pressure of gas that instrument 6 will attempt to maintain in the inflatable portion of cuff 10 when cuff 10 is inflated. Controller 32 will generate high or low pressure alarm signals if the pressure in cuff 10 cannot be maintained near the selected reference pressure level. If the cuff pressure level exceeds the reference pressure level by 15 mmHg a high pressure alarm signal will be generated by controller 32. If the cuff pressure level falls below the reference pressure level by 15 mmHg a low pressure alarm signal will be generated by controller 32.

When controller 32 detects that the "inflate" key on keypad 26 has been depressed by the operator of instrument 6, controller 32 operates to inflate cuff 10 to a pressure near the selected reference pressure level and to then regulate the pressure in cuff 10 near the reference pressure level until such time that controller 32 detects that the "deflate" key on keypad 26 has been depressed by the operator of instrument 6. Controller 32 may also inflate, adjust the reference pressure level, and deflate cuff 10 automatically during a limb occlusion pressure measurement as described further below.

To inflate and regulate the pressure in cuff 10 controller 32 includes a pressure regulator; the pressure regulator in the preferred embodiment is implemented as a control algorithm that operates as described below. At regular predetermined regulation intervals of 40 ms controller 32 computes a pressure error signal. The pressure error signal corresponds to the difference between the reference pressure level and the cuff pressure level. Controller 32 uses the pressure error signal as a term in a proportional integral control algorithm to calculate activation time intervals for inflation valve 44 and deflation valve 50. To increase the gas pressure in cuff 10 when the cuff pressure signal is below the reference pressure level, the activation time interval for deflation valve 50 is set to zero and the activation time interval for inflation valve 44 is proportional to the magnitude of the pressure error signal and the integral of the pressure error signal. To decrease the gas pressure in cuff 10 when the cuff pressure signal is above the reference pressure level, the activation time interval for inflation valve 44 is set to zero and the activation time interval for deflation valve 50 is proportional to the magnitude of the pressure error signal and the integral of the pressure error signal. Controller 32 limits the maximum valve activation time intervals of valve 44 and valve 50 to the regulation interval time (40 ms). It will be appreciated by those skilled in the art that alternate pressure regulation algorithms could be employed to control the activation of inflation valve 44 and deflation valve 50 in response to a cuff pressure signal and a reference pressure level, or that proportional valves could be used instead of the valves used in the preferred embodiment. Also it will be appreciated that a regulator has a response time, consisting of the amount of time required for the pressure of gas in the cuff to reach the level of the reference pressure level after a new reference pressure level has been selected. The regulator response time will depend upon the magnitude of the change in reference pressure level, the volume of cuff 10 and the characteristics of the pneumatic components in instrument 6 and the specifics of the control algorithm used. Thus the actual pressure of gas in cuff 10 may differ substantially from the reference pressure level for a varying period of time after a change in the reference pressure level.

Figure 3:
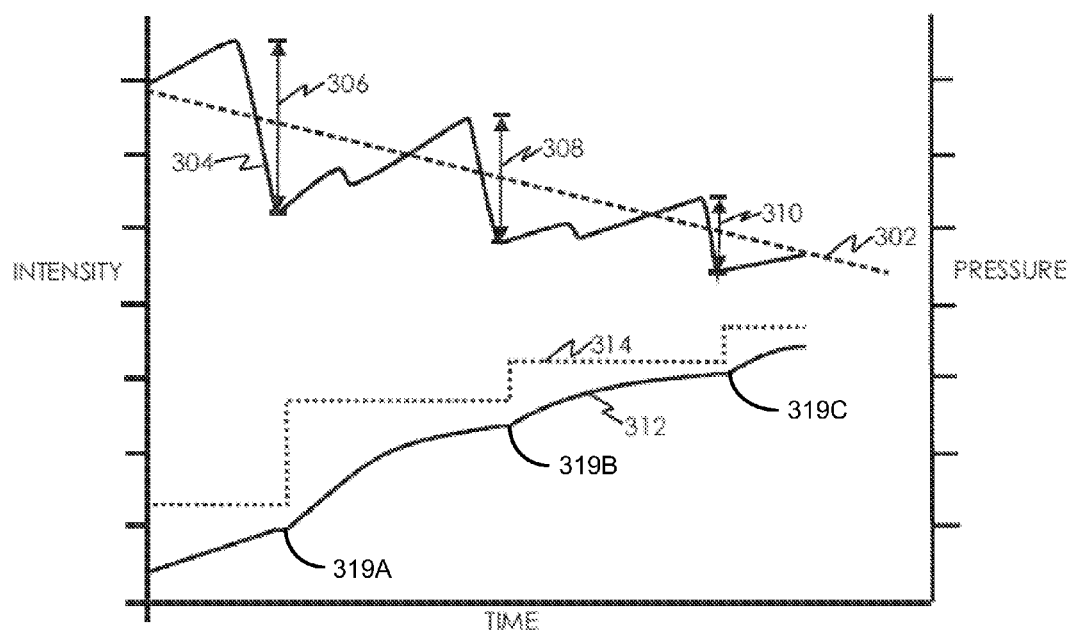
FIG. 3 is an illustration that shows increases in the level of the cuff reference pressure in synchrony with arterial pulsations detected during the measurement of limb occlusion pressure by the preferred embodiment.

In order to correctly regulate the pressure of gas in cuff 10 at a pressure near the cuff pressure reference level and correctly indicate over and under pressure alarm conditions, controller 32 must have available an indication of the pressure within the inflatable portion of cuff 10. In the preferred embodiment the measurement of the pressure of gas in cuff 10 is facilitated by cuff pressure transducer 52 and the direct pneumatic connection between the inflatable portion of cuff 10 and transducer 52. Gas flow in the pneumatic passageway connecting cuff pressure transducer 52 with the inflatable portion of cuff 10 caused by the opening of inflation valve 44 and deflation valve 50 produces error in the cuff pressure measurement made by pressure transducer 52. An accurate measurement of the pressure of gas in cuff 10 is critical to the ability of instrument 6 to accurately and rapidly measure LOP, as explained below. During a measurement of LOP, and upon the detection of an arterial pulsation in blood flow, controller 32 closes deflation valve 50 and inflation valve 44 to suspend pressure regulation for a predetermined time period (typically 30 ms); this temporary suspension of pressure regulation in a single-port tourniquet system enables an accurate measurement of cuff pressure near the time that the arterial pulsation occurred. In a representative implementation as depicted in FIG. 3, the temporary suspension of pressure is shown at intervals 319A, 319B and 319C on a curve 312 representing the cuff pressure.

Blood Flow Transducer and Signal Processing

Referring again to FIG. 2, the internal components of blood flow transducer 2 are shown in detail. Blood flow transducer 2 of the preferred embodiment employs the principle of photoplethysmography and is adapted for positioning on the limb distal to the tourniquet cuff, although it will be appreciated that other types of blood flow transducers employing other principles may be used, and it will be appreciated that some types of blood flow transducers may be physically integrated into the structure of a tourniquet cuff. In the preferred embodiment, blood flow transducer 2 has a hinged plastic housing that is configured for application to a digit of a limb. Blood flow transducer 2 may be applied to a finger or thumb of the hand or a toe of the foot. Transducer 2 includes an infrared light emitting diode (IRLED) 60 and a photodiode 62 which is sensitive to the wavelength of light emitted by IRLED 60. In the preferred embodiment an IRLED with a wavelength of 915 nm is employed. Within blood flow transducer 2 IRLED 60 and photodiode 62 are positioned directly opposite each other such that light emitted by IRLED 60 is readily detected by photodiode 62. When applied to a digit IRLED 60 illuminates a volume of tissue and photodiode 62 detects the light that is transmitted through this volume of tissue.

IRLED 60 is connected via multi-conductor cable 8 to adjustable constant current source 64. The intensity of light emitted by IRLED 60 is proportional to the amount of electrical current that flows through IRLED 60. Controller 32 communicates with adjustable constant current source 64 to set the level of current that flows through IRLED 60 and thereby the intensity of light emitted by IRLED 60. In the preferred embodiment the current source 64 can be adjusted to supply electrical current ranging from 0 to 100 milliamps in steps of 0.1 milliamps by controller 32.

Photodiode 62 generates an electrical current that is linearly proportional to the intensity of light that strikes the light sensitive area of photodiode 62. Photodiode 62 is connected by multi-conductor cable 8 to blood flow signal processor 66. Signal processor 66 amplifies, filters, and digitizes the current generated by photodiode 62 to produce a blood flow signal that is representative of the intensity of light that strikes photodiode 62. The characteristics of photodiode 62 and the electronic circuits within signal processor 66 determine the minimum and maximum light intensities that the blood flow signal can represent. As described below, the preferred embodiment operates to maintain the level of the blood flow signal within the dynamic range of signal processor 66.

When blood flow transducer 2 is applied to a digit of a patient's limb the intensity of light reaching photodiode 62 is dependent upon a number of factors. These factors are the initial intensity of the light emitted by IRLED 60; the amount of light absorbed by the skin pigmentation, tissue and bone of the digit; the amount of light absorbed by venous blood and non-pulsatile arterial blood and pulsatile arterial blood; and the optical path length between IRLED 60 and photodiode 62. When cuff 10 is deflated, a relatively constant amount of light is absorbed by the skin pigmentation, bone other tissue, venous blood and the non-pulsatile part of the arterial blood. This aggregate non-pulsatile component of the blood flow signal, illustrated as non-pulsatile signal 302 in FIG. 3, is detected and measured by non-pulsatile level detector 68. Non-pulsatile level detector 68 communicates to controller 32 the level of non-pulsatile signal 302.

During each cardiac cycle the diameters of the arteries and arterioles alternately increase and decrease in response to arterial blood flow pulsations. This alternating increase and decrease in diameters affects the optical path length between IRLED 60 and photodiode 62 and produces a rhythmical and alternating variation in the intensity of light transmitted through the digit that is in synchrony with each cardiac cycle. Typically, this rhythmical and alternating variation of intensity is 1-2 percent of the total amount of light transmitted through the volume of tissue, and results in the production by signal processor 66 of a blood flow signal having alternating variations as illustrated in FIG. 3. Arterial pulsation detector 70 detects an arterial pulsation by detecting the occurrence of the alternating variation in the blood flow signal from signal processor 66 that occurs during each cardiac cycle, and further determines the relative magnitude of each detected arterial pulsation by determining the difference between the minimum and maximum of each alternating variation of the blood flow signal, as illustrated in FIG. 3.

FIG. 3 illustrates non-pulsatile signal 302, blood flow signal 304, and arterial pulsations of magnitudes 306, 308 and 310 that decrease as cuff pressure 312 increases in response to increases in reference pressure level 314. FIG. 3 also illustrates that cuff pressure 312 may differ significantly from reference pressure level 314 for varying periods of time after changes in reference pressure level 314. Finally, FIG. 3 illustrates that, in the preferred embodiment, changes in reference pressure level 314 are only made in synchrony with arterial pulsations detected by arterial pulsation detector 70, as explained further below. Synchronizing any change in reference pressure level 314 to detected arterial pulsations is an important characteristic of the preferred embodiment that greatly increases the speed of LOP measurement in comparison to prior-art apparatus in which increases in reference pressure levels are made at arbitrary, unsynchronized times.

The magnitude is affected by the intensity of light emitted by IRLED 60. Generally, as the intensity of light emitted by IRLED 60 increases, the volume of tissue illuminated by IRLED 60 increases which results in an increase in the magnitude of the alternating and rhythmical variation of the blood flow signal as more arteries and arterioles are illuminated in the optical path between IRLED 60 and photodiode 62.

The optical path length through the volume of tissue between IRLED 60 and photodiode 62 is also affected by any change in diameter of the venules and the amount of venous blood in the tissue. When cuff 10 is pressurized to a level that is greater than that required to occlude venous blood from flowing out of the limb but still at a level that allows arterial blood to flow into the limb there is an increase in the volume of venous blood present in the limb and a corresponding increase in the diameter of the venules. This increase in diameter increases the optical path length through the volume of tissue and results in a decrease in the amount of light detected by photodiode 62. This decrease in light intensity happens gradually, but may be substantial, resulting in reductions of up to three orders of magnitude of the light transmitted through the volume of tissue. In the preferred embodiment this change in the intensity of light transmitted through the volume of tissue is compensated for by an increase in the intensity of IRLED 60, as described further below. In some circumstances described further below it may not be possible to compensate for this magnitude of change in intensity as IRLED 60 has an upper limit to the intensity of light that it can produce.

Each cardiac cycle that occurs when cuff 10 is at a pressure that partially or completely stops venous outflow, but not arterial inflow, results in an increase in the amount of venous blood in the volume of tissue illuminated by IRLED 60. It is important to minimize the time that cuff 10 is at these pressures because the accumulation of venous blood may be hazardous, as explained above. It is also important that this time be minimized to ensure that the photoplethysmographic blood flow signal remains in a region that is within the dynamic range of IRLED 60 to illuminate the tissue, and within the dynamic range of the electronic circuits used to detect and process the signal from photodiode 62. The preferred embodiment acts to minimize the time that cuff 10 is at these pressures when attempting to make a measurement of LOP by assessing during an initialization period whether such an attempted measurement is likely to be successful, as follows. In the initialization period, if a blood flow signal cannot be detected by signal processor 66, or if alternating rhythmical variations of the blood flow signal characterizing arterial pulsations above a predetermined minimum initial magnitude cannot be detected by arterial pulsation detector 70, then controller 32 increases the intensity of IRLED 60 by adjusting the current to IRLED 60 by means of adjustable constant current source 68 in an effort to increase the magnitude of the blood flow signal to a level suitable for analysis. If this adjustment by current source 64 still does not result in a blood flow signal having variations greater than the predetermined minimum initial magnitude, then controller 32 promptly terminates the attempt to measure LOP and produces an appropriate indication perceptible to the operator. In this way, the preferred embodiment minimizes the duration of an attempt to measure LOP that may delay the start of surgery, and that may cause venous blood pooling, if that measurement of LOP is unlikely to be successfully completed, and allows the operator to promptly select another reference pressure level for the tourniquet system that is not based on LOP.

If an attempt to measure LOP has not been terminated during the initialization period, arterial pulsation detector 70 continues to analyze the blood flow signal from signal processor 66 to detect the occurrence of each alternating rhythmical variation above a minimum detection threshold that characterizes an arterial pulsation of blood flow, and to indicate to controller 32 the magnitude of the difference between the maximum and minimum of the alternating rhythmical variation, as illustrated by magnitudes 306, 308 and 310 in FIG. 3. Each magnitude is representative of the amount of arterial blood flowing into the volume of tissue between IRLED 60 and photodiode 62 during the period of each cardiac cycle. To be correctly identified as an arterial pulsation of blood flow, the magnitude must exceed the minimum detection threshold. The minimum detection threshold of arterial pulsation detector 70 is initially set to a predetermined threshold, and may subsequently be set by controller 32 to another threshold.

When an arterial pulsation is detected by arterial pulsation detector 70, the time of occurrence is communicated to controller 32, and pulsation detector 70 enters a refractory time period immediately after the detected occurrence. During the refractory time period, pulsation detector 70 is non-responsive to the blood flow signal from signal processor 66. This non-responsiveness of pulsation detector 70 to the blood flow signal during the refractory time period allows controller 32 to make adjustments to the level of the current supplied by adjustable constant current source 64 to IRLED 60 while preventing pulsation detector 70 from erroneously analyzing any noise or artifact in the blood flow signal resulting from the adjustments to the level of current to IRLED 60. During the measurement of LOP, controller 32 typically sets the refractory time period of pulsation detector 70 to be equal to 75 percent of the time between successively detected arterial pulsations. Depending on the time between successive pulsations, the duration of the refractory time period may be adjusted by controller 32 from a predetermined initial time of 350 milliseconds to a predetermined maximum time of 1200 milliseconds. As described above, during measurement of LOP, controller 32 suspends pressure regulation in response detection of an arterial pulsation and closes deflation valve 50 and inflation valve 44 for a time period sufficient for an accurate measurement of cuff pressure near the time of the arterial pulsation.

Instrument 6 includes blood flow signal quality indicator 12 to provide the operator with an indication that blood flow transducer 2 has been correctly applied to a digit of patient limb 4 and that a blood flow signal exceeding predetermined minimum quality criteria described below is being obtained.

As shown in FIG. 2, instrument 6 includes a blood flow signal quality processor 72 that evaluates the blood flow signal quality. For clarity, blood flow signal quality processor 72 has been shown as a separate functional block in FIG. 2, although the function performed by blood flow signal quality processor 72 may be implemented as software algorithms performed by controller 32. Blood flow signal quality processor 72 controls the activation of blood flow signal quality indicator 12, and enables or inhibits the automatic measurement of LOP in response to the activation of LOP key 14 or LOP key 30.

Figure 4:
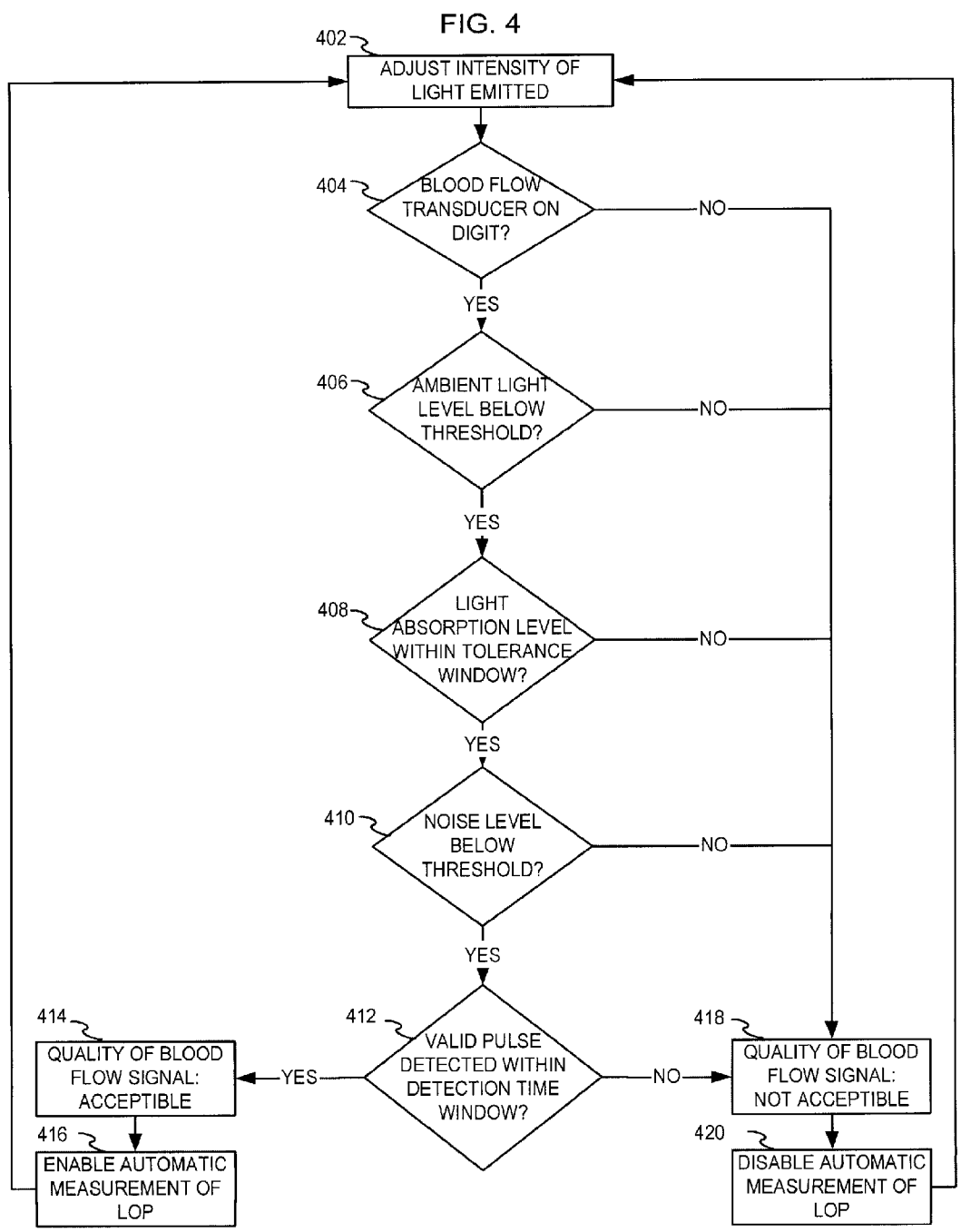
FIG. 4 is a flow chart depicting the sequence of operations performed to evaluate blood flow signal quality.

Blood flow signal quality processor 72 evaluates the blood flow signal quality by continuously monitoring several key characteristics of the blood flow signal that affect the signal quality. Referring to FIG. 4, the evaluation algorithm employed by blood flow signal quality processor 72 is shown in detail. The algorithm begins by temporarily adjusting the intensity of light emitted by IRLED 60 to a predetermined minimum level (402), and then determines if blood flow transducer 2 is attached to a digit by monitoring the level of the non-pulsatile signal from non-pulsatile level detector 68 (404). If blood flow transducer 2 is not attached to a digit, the level of the non-pulsatile signal will exceed a predetermined threshold due to the saturation of photodiode 62 by light emitted by IRLED 60; otherwise, the algorithm proceeds to verify that the level of ambient light detected is below a predetermined threshold (406).

To determine if the level of ambient light at blood flow transducer 2 is excessive and may interfere with the measurement of blood flow, blood flow signal quality processor 72 temporarily switches off IRLED 60, then acquires the level of the non-pulsatile signal from non-pulsatile level detector 68 and then compares the level to a predetermined ambient light threshold. Excessive ambient light detected at blood flow transducer 2 may be caused by direct illumination from surgical lighting, by poor contact between transducer 2 and the digit, or by a combination of both factors. If the level of ambient light is below the predetermined ambient light threshold, the algorithm proceeds to verify that the amount of light absorbed by the digit is within a predetermined absorption tolerance window (408). The light absorption level is determined by observing the change in the level of non-pulsatile signal resulting from a variation in the electrical current supplied to IRLED 60 and thereby the intensity of IRLED 60. In a digit with normal light absorption characteristics, a change in the level of non-pulsatile signal is proportional to the change in electrical current supplied to IRLED 60. Factors that may affect the light absorption characteristics of a digit include skin pigmentation, volume and biological structure. For example, if the patient has a thick digit, the light absorbed may exceed a predetermined maximum absorption level, and thus potentially affect the detection of pulsatile signals during the measurement of LOP. Other non-patient related causes of suboptimal non-pulsatile signal level may include poor coupling between the surface of the digit and IRLED 60 and photodiode 62, excessive preparation solution obstructing IRLED 60 or photodiode 62, poor positioning of blood flow transducer 2, and poor cleaning of blood flow transducer 2 before use.

The algorithm next verifies that the noise level of the blood flow signal is below a predetermined noise threshold (410). In the preferred embodiment this is done by detecting the number of zero-crossings and slope changes that occur in the blood flow signal over a predetermined time period, however it will be appreciated that other methods may be used to quantify signal noise. In an intraoperative environment, sources of noise may originate from the patient having a cold digit that leads to low perfusion, movement of the patient such as shivering, activities from surgical staff preparing the limb, and electrical noise from other equipment in the operating room that may interfere with blood flow transducer 2.

Next, the algorithm determines if an arterial pulsation having a predetermined minimum magnitude can be detected within a predetermined detection time window (412). A low magnitude arterial pulsation can be caused by poor perfusion, a cold digit, limb elevation, and improper positioning of blood flow transducer 2 on the digit. If the magnitude of the detected arterial pulsation is greater than the predetermined minimum magnitude, and if the arterial pulsation occurs within the predetermined time window (412), blood flow signal quality processor 72 determines that the blood flow signal quality is acceptable (414), illuminates the blood flow quality indicator 12 green LED and enables the automatic measurement of LOP (416). If the blood flow signal does not meet any of the conditions described above, blood flow signal quality processor 72 determines that the blood flow signal quality is not acceptable (418), illuminates the blood flow quality indicator 12 red LED, and inhibits the automatic measurement of LOP (420). An indication of blood flow signal quality is also provided on display 24.

It will be appreciated that additional criteria may be used by blood flow signal quality processor 72 in evaluating signal quality; for example, a force sensor could be integrated into blood flow transducer 2 to measure the force applied to the patient's digit by blood flow transducer 2. Signals from the force sensor could be used to further augment the blood flow signal quality determination by providing an indication of when excess force is applied to the region of the digit to which blood flow transducer 2 is applied. Excessive force applied by blood flow transducer 2 may lead to an unsuccessful or inaccurate LOP measurement due to reduced vascular blood flow.

Limb Occlusion Pressure Measurement

To automatically measure the limb occlusion pressure, controller 32 must determine the minimum pressure required in cuff 10 to prevent arterial blood flow into patient limb 4 distal to the location of cuff 10. As described in detail below, controller 32 does this by analyzing signals produced by non-pulsatile level detector 68, by arterial pulsation detector 70 and by blood flow signal processor 66 while increasing the pressure in cuff 10 to a pressure level at which arterial blood flow is no longer detectable above a minimum detection threshold.

Figure 5:
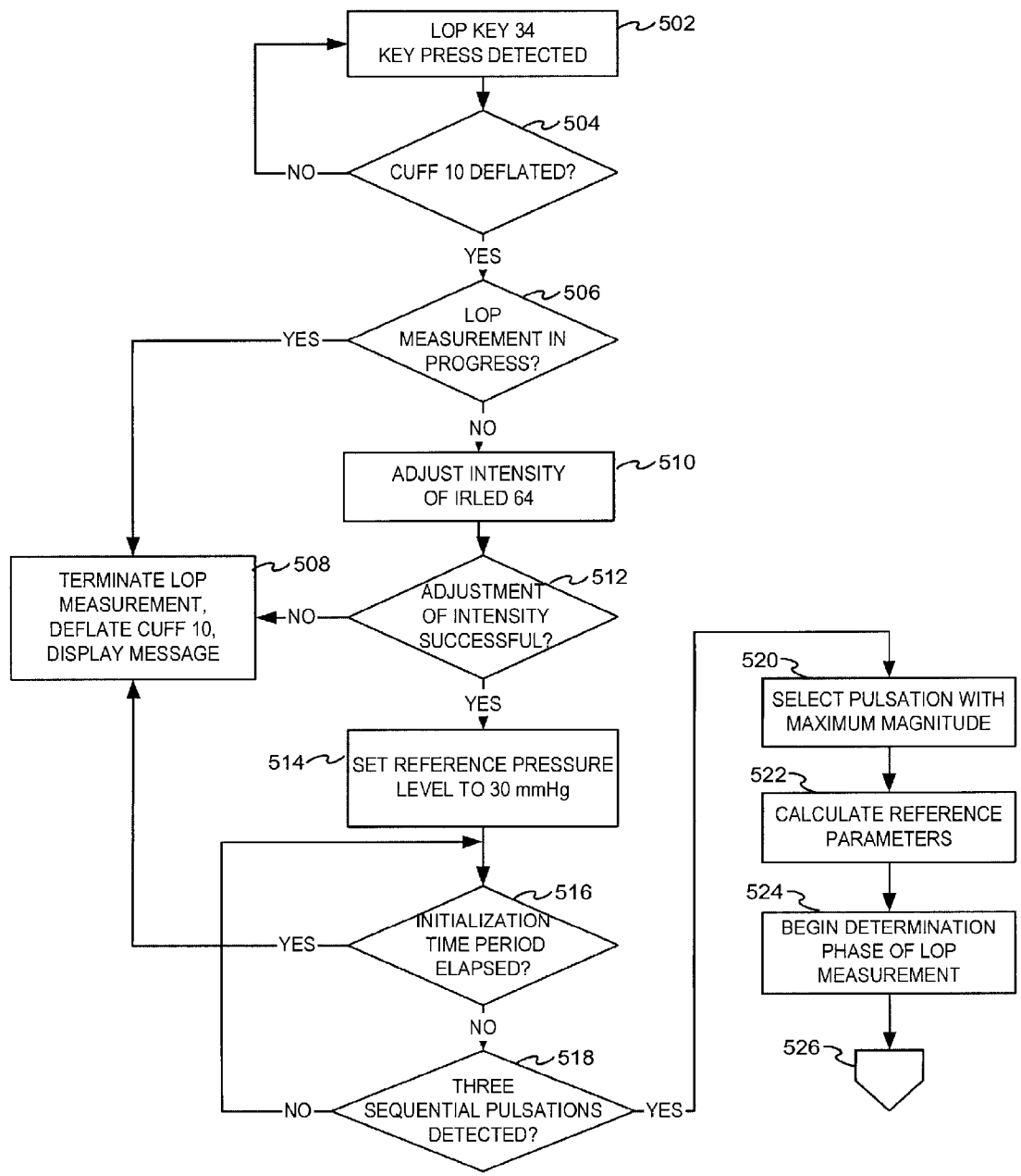
FIG. 5 and FIG. 6 are flow charts depicting the sequence of operations performed by the preferred embodiment during measurement of limb occlusion pressure.
Figure 6:
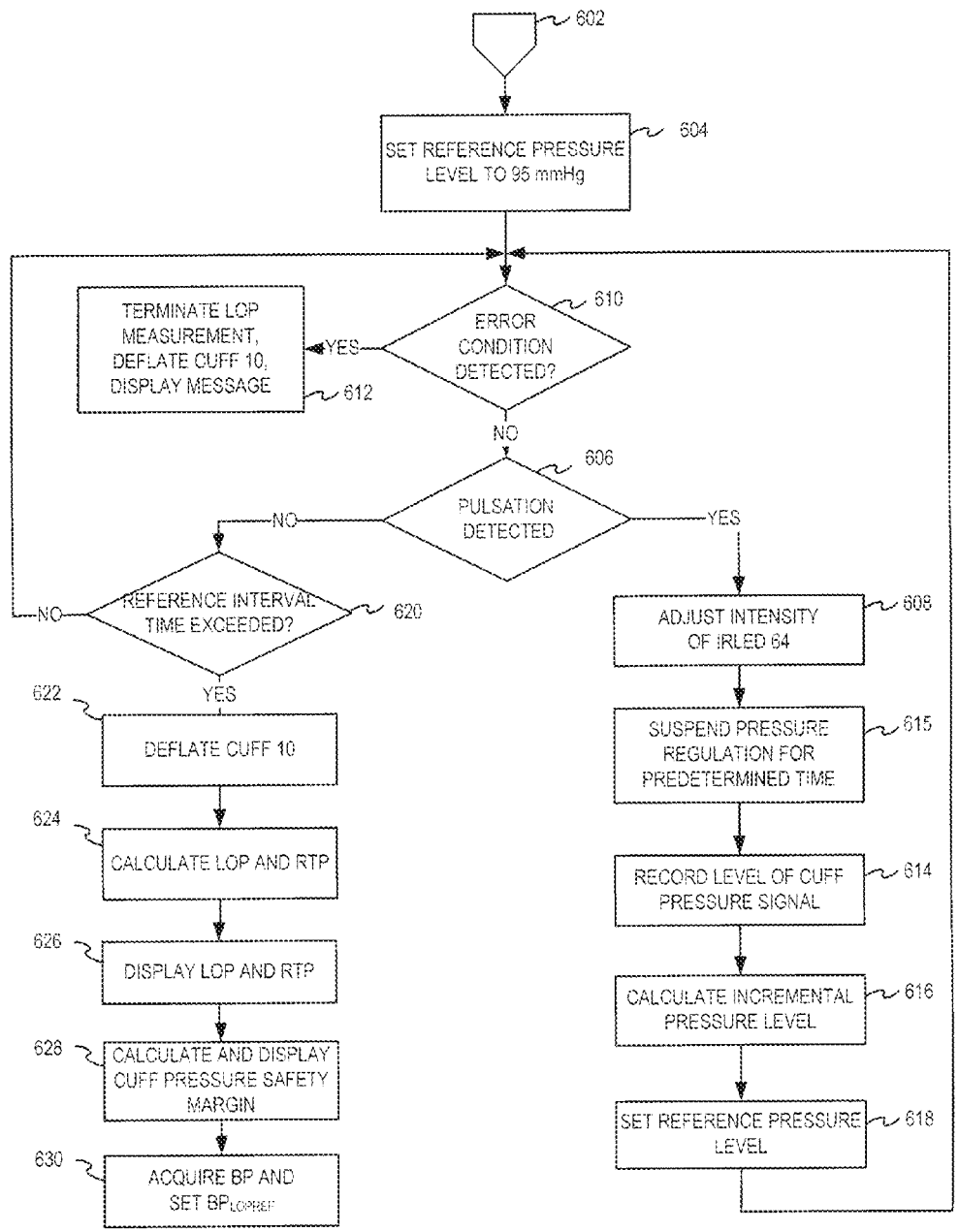

To enable a better understanding of the sequence of operations completed and decisions made by controller 32 during the automatic measurement of limb occlusion pressure a flow chart is provided in FIG. 5 and FIG. 6.

Referring to the flow chart in FIG. 5, when controller 32 detects that LOP key 30 on keypad 26 or LOP key 14 on blood flow transducer 2 has been depressed and the measurement of LOP has not been inhibited by blood flow signal quality processor 72 (502) it first determines if cuff 10 is already inflated and being regulated as would be the case if the operator of instrument had previously activated the inflate key on keypad 26 (504). Controller 32 only responds to LOP key 30 or LOP key 14 to initiate an LOP measurement sequence when cuff 10 is deflated and controller 32 is not regulating the gas pressure within cuff 10. This safety feature of the preferred embodiment prevents the operator from inadvertently initiating a measurement of LOP at a time when a surgical procedure may be in progress.

If controller 32 detects that LOP key 14 on blood flow transducer 2, or LOP key 30, or any other key on keypad 26 has been depressed while an LOP measurement sequence is in progress, controller 32 terminates the LOP measurement (506). An appropriate alarm message is shown on display panel 24 and controller 32 activates deflation valve 50 to vent gas from cuff 10 (508). This allows the operator of instrument 6 to safely cancel an LOP measurement sequence that is in progress.

The LOP measurement sequence performed by controller 32 has two phases: an initialization phase during an initialization time period when reference parameters are established; and a determination phase during which the reference pressure level is monotonically increased until the pressure in cuff 10 reaches the limb occlusion pressure.

The initialization phase of the sequence for measuring LOP begins with controller 32 adjusting the intensity of IRLED 60 by communicating with constant current source 64 (510). The intensity of IRLED 60 is set to a level that produces a non-pulsatile photoplethysmographic signal at a level indicated by non-pulsatile level detector 68 that is near a predetermined initial target level.

If the non-pulsatile photoplethysmographic signal cannot be set to a level that is near the initial target level, such as may be the case if blood flow transducer 2 is applied to a very thick digit or a to digit that for other reasons absorbs a significant portion of the light emitted by IRLED 60 (512), controller 32 determines that the LOP measurement sequence is unlikely to successfully complete, terminates the measurement attempt, and displays an appropriate message on display panel 24 (508). Also, if the amount of current that is required from constant current source 64 to produce a non-pulsatile photoplethysmographic signal at a level near the initial target level exceeds a predetermined maximum, then controller 32 also determines that the LOP measurement sequence is unlikely to successfully complete because there will be insufficient adjustment range available to further increase the intensity of IRLED 60 to compensate for changes in venous blood volume that may occur during the measurement.

Next, controller 32 sets the reference pressure level to a predetermined initial level of 30 mmHg (514). The pressure regulator then commences inflation of cuff 10 to a pressure near 30 mmHg.

Controller 32 then waits for a predetermined maximum time period of 5 seconds (516) for arterial pulsation detector 70 to detect three sequential blood flow pulsations with a magnitude greater than a predetermined minimum initial magnitude (518). If three sequential pulsations that exceed the minimum initial magnitude are not detected within the predetermined maximum time period, indicating that the LOP measurement attempt is unlikely to be successfully completed, then the LOP measurement sequence is terminated and the reference pressure level is set to zero to start the deflation of cuff 10. A message is displayed on display panel 24 to alert the operator that an LOP measurement could not be completed (508), thus minimizing the duration of an LOP measurement attempt that might be unsuccessful and that might delay the start of surgery and lead to excessive accumulation of venous blood.

If arterial pulsation detector 70 detects three sequential arterial blood flow pulsations that exceed the predetermined minimum initial magnitude, controller 32 calculates the levels of reference parameters to be used in the determination phase of the LOP measurement sequence. Controller 32 chooses from the three sequentially detected pulsations the pulsation with the greatest magnitude (520), and the magnitude of this pulsation is selected by controller 32 as the reference magnitude. As described below, controller 32 makes comparisons of the magnitude of subsequent pulsations to the reference magnitude. Controller 32 calculates a reference pulsation interval time which is the time interval between two of the three detected successive arterial pulsations (522). Controller 32 sets the refractory period of arterial pulsation detector 74 to 75 percent of the calculated reference pulsation interval time. Controller 32 also calculates the minimum detection threshold and communicates this threshold to arterial pulsation detector 70. As described above, the minimum detection threshold determines the minimum magnitude of an arterial pulsation that is detected by arterial pulsation detector 70. In the preferred embodiment, controller 32 computes the minimum detection threshold to be the greater of 5 percent of the reference magnitude and a predetermined minimum threshold.

Controller 32 next enters the determination phase of the LOP measurement sequence (524). The flow chart shown in FIG. 5 continues (526) in FIG. 6 (602). FIG. 6 depicts the determination phase of the LOP measurement sequence; controller 32 begins by setting the reference pressure level to a predetermined level of 95 mmHg (604). Controller 32 compensates for changes in the amount of venous blood present in the volume of tissue between IRLED 60 and photodiode 62 that may occur during the determination phase of the LOP measurement sequence as follows. Each time an arterial blood flow pulsation is detected by arterial pulsation detector 70 (606), controller 32 computes a new level for adjustable constant source 64 and thereby the intensity of IRLED 60. Controller 32 uses a proportional control algorithm to calculate a new level for constant current source 64 that maintains the level of the non-pulsatile photoplethysmographic signal from non-pulsatile level detector 68 near the target level set previously (608). The change to the intensity of IRLED 60 is made during the refractory period of arterial pulsation detector 70 so that artifacts that are caused by changing of the intensity of IRLED 60 do not affect arterial pulsation detector 70. By continuously updating the level of constant current source 64 after each arterial pulsation is detected in response to changes in the non-pulsatile signal level, controller 32 can compensate for changes in the absorption of light emitted by IRLED 60 due to changes in the amount of venous blood present in the volume of tissue illuminated by IRLED 60 and maintain the non-pulsatile photoplethysmographic signal near the target level.

If during LOP measurement controller 32 detects that the level of the non-pulsatile signal from non-pulsatile level detector 68 has exceeded a predetermined minimum or maximum limit level (610) controller 32 terminates the LOP measurement and opens deflation valve 50 to deflate cuff 10 (612). Examples of conditions that may cause the non-pulsatile signal to exceed the limits are the inadvertent removal of blood flow transducer 2 from the digit during the measurement, an excessive amount of venous blood accumulating in the digit, failure of the multi-conductor cable 8, or failure of transducer 2. Controller 32 also notifies the operator by displaying an appropriate alarm message on display panel 24 and by audio tones produced by speaker 54.

To increase the pressure in cuff 10 as rapidly as possible to the LOP, and at the same time to provide an accurate measurement of LOP, controller 32 operates as follows. Each time an arterial blood flow pulsation is detected by arterial pulsation detector 70 a new reference pressure level is calculated by controller 32. Near the time that the pulsation is detected, controller 32 records the level of the cuff pressure signal (614); this represents the pressure of gas in cuff 10 near the time that the blood flow pulsation occurred. To ensure the cuff pressure signal accurately reflects the pressure of gas in the inflatable portion of cuff 10, pressure regulation is suspended (615) near the time that the blood flow pulsation occurs, as described above. Based on the magnitude of the detected blood flow pulsation in comparison with the reference magnitude an incremental pressure level is calculated (616). Shortly after the detection of the blood flow pulsation and thus in synchrony with the pulsation, the reference pressure level is set by controller 32 to a level equal to the sum of the calculated incremental pressure level and the recorded cuff pressure level (618).

During the measurement of LOP, the magnitude of a detected arterial blood flow pulsation is dependent upon the pressure in cuff 10 at the time the pulsation occurs. As the pressure in cuff 10 nears the pressure required to totally occlude arterial blood flow, the magnitudes of arterial blood flow pulsations are reduced. To enable the preferred embodiment to rapidly increase the pressure in cuff 10 to the minimum pressure that occludes arterial blood flow, while not increasing the pressure in cuff 10 above that minimum pressure, the size of the pressure increment that is made after each detected arterial pulsation is dependent on the magnitude of the detected arterial blood flow pulsation. By making progressively smaller increments in pressure for cuff 10 as the cuff pressure nears the LOP, the preferred embodiment can make a very rapid and accurate determination of LOP.

In the preferred embodiment, the incremental pressure level is calculated as follows: 15 mmHg for a pulsation with a magnitude of 66 percent of the reference magnitude or greater; 10 mmHg for a pulsation with a magnitude of 50-65 percent of the reference magnitude; 7 mmHg for a pulsation with a magnitude of 33-49 percent of the reference magnitude; 5 mmHg for a pulsation with a magnitude of 20-32 percent of the reference magnitude; and 3 mmHg for a pulsation with a magnitude of less than 20 percent of the reference magnitude.

By making each increased reference pressure level equal to the sum of the calculated incremental pressure level that is based on the magnitude of an arterial pulsation plus the recorded cuff pressure level (614) at the time of that pulsation, and by increasing the reference pressure level in synchrony with that pulsation, the LOP measurement can proceed rapidly, accurately, and independently of the response time characteristic of the pressure regulator in combination with the pneumatic elements of the preferred embodiment. As an example, if the cuff pressure signal corresponds to a level of 133 mmHg when a pulsation is detected, and if the magnitude of the detected pulsation relative to the reference magnitude is greater than 66 percent, then controller 32 sets the reference pressure level to 148 mmHg (133+15) shortly after the pulsation. This is a more rapid and more accurate way to approach the true LOP in comparison to prior art apparatus in which each increased reference pressure level is typically determined by adding a predetermined increment to the previous reference pressure level, and in which the reference pressure level is increased only after sufficient time has elapsed to allow actual cuff pressure to reach the previous reference pressure level.

Referring again to FIG. 6, controller 32 continues to increase the reference pressure level each time a arterial blood flow pulsation is detected by arterial pulsation detector 70 until an arterial blood flow pulsation is not detected for a period of time that is two times the reference pulsation to pulsation interval time determined during the initialization phase of the LOP measurement sequence (620). When during the determination phase of the LOP measurement sequence an arterial blood flow pulsation is not detected for this period of time, controller 32 calculates the limb occlusion pressure to be the pressure of gas in cuff 10 as represented by the cuff pressure signal.

Controller 32 then deflates cuff 10 by setting the reference pressure level to zero and activating deflation valve 50 (622). Controller 32 then calculates the recommended tourniquet pressure as described below (624) and displays the results of the LOP measurement on display panel 24, this completes the LOP measurement sequence (626).

When the LOP has been determined controller 32 calculates a recommended tourniquet pressure (RTP) by adding a predetermined offset pressure level (margin of safety) to the LOP. In the preferred embodiment the offsets added to the LOP to calculate an RTP are consistent with recommendations from the surgical literature and are calculated as follows: if the LOP is greater than 190 mmHg the RTP is calculated by adding 100 mmHg to the LOP; if the LOP is greater than 130 mmHg the RTP is calculated by adding 75 mmHg to the LOP; or if the LOP is less that 131 mmHg the RTP is calculated by adding 50 mmHg to the LOP.

Controller 32 displays the measured LOP and the calculated RTP on display panel 24 and indicates that the measurement is complete. For example, if instrument 6 measures an LOP of 145 mmHg, then an RTP of 220 mmHg is calculated and both the LOP and RTP are shown on display panel 24. An operator may select the displayed RTP to be the reference pressure level or may manually select a different reference pressure level that is not based on LOP.

In the preferred embodiment, the difference in pressure between the selected reference pressure (RP), which may be the RTP, and the measured LOP is defined as the Cuff Pressure Safety Margin (SM) {SM=RP−LOP}. The Cuff Pressure Safety Margin is automatically computed by controller 32 and the computed value is shown on display panel 24 of instrument 6 (628).

The systolic blood pressure of the patient is one factor that has been shown to affect the measured LOP. Changes in blood pressure that occur subsequent to the measurement of LOP due to the effects of anesthesia and other factors have an effect on the value of the Cuff Pressure Safety Margin. To alert the operator to a change in the value of Cuff pressure Safety Margin instrument 6 computes and displays an Updated Cuff Pressure Safety margin $SM_U$) when the patient's blood pressure can be obtained from an external patient monitor by physiologic characteristic acquisition module 56 near the time of the LOP measurement and subsequently while cuff 10 is pressurized.

In the preferred embodiment, within a predetermined minimum time of the completion of an LOP measurement, the results of a non-invasive or real time blood pressure measurement from an external patient monitor are acquired by physiologic characteristic acquisition module 56 (630) to establish an LOP Reference Blood Pressure ($BP_{LOPREF}$). If the results of a recent blood pressure measurement are not available from an external patient monitor, controller 32 via physiologic characteristic acquisition module 56 may instruct the external patient monitor to perform a blood pressure measurement and obtain the resulting data to establish a $BP_{LOPREF}$.

To compute the value of the Updated Cuff Pressure Safety Margin when cuff 10 is pressurized to occlude blood flow subsequent to the measurement of LOP, controller 32 automatically obtains the values of recent patient systolic blood pressure measurements (BP) via physiologic characteristic acquisition module 56. In the preferred embodiment, the Updated Cuff Pressure Safety Margin is computed by the formula $\{SM_U=RP-LOP+k(BP_{LOPREF}-BP)\}$, where k is a constant value of 1.1. This relationship between Updated Cuff Pressure Safety Margin, blood pressure and LOP has been chosen based on empirical data available at present. It will be appreciated that other mathematical relationships may be used to determine the value of the Updated Cuff Pressure Safety Margin.

The preferred embodiment includes means for the operator to increase or decrease the reference pressure upon consideration of the displayed value of the Updated Cuff Pressure Safety Margin. The preferred embodiment also includes a Safety Margin Alarm Limit Window that may be automatically set at predetermined levels above and below the Cuff Pressure Safety Margin by controller 32, or that may be set by the operator of instrument 6 to desired levels above and below the Cuff Pressure Safety Margin. If the Updated Cuff Pressure Safety Margin exceeds the levels set by the Safety Margin Alarm Limit Window, the operator of instrument 6 is alerted by an audible sound produced by speaker 54 and by a message shown on display panel 24.

Typical Use in Surgery

To enable a better understanding of the preferred embodiment, its typical use in a surgical procedure is described below.

An operator first selects an appropriately sized cuff 10 for application to patient limb 4 and secures cuff 10 around patient limb 4. The pneumatic passageway from instrument 6 to the inflatable portion of cuff 10 is completed by mating connectors 18 and 20. Many different sizes and shapes of cuff 10 may be optionally used with instrument 6 to accommodate different physical sizes of patients and patient limbs. Cuffs may vary in length, width, shape, and application technique; also some cuffs may be applied with a soft limb protection sleeve located between the limb and the cuff. The specific level of pressure required in tourniquet cuff 10 to stop blood flow past cuff 10 at a particular time is affected by variables including the characteristics of cuff 10 and any underlying sleeve, the technique used in applying cuff 10, the physiological characteristics of the patient, and the physical characteristics of limb 4 at the location where cuff 10 is applied.

Accordingly, to assist in setting the reference pressure to the lowest and safest level, the operator of instrument 6 may choose to initiate a measurement of LOP. To perform a rapid and accurate measurement of LOP the operator first applies blood flow transducer 2 to a digit of patient limb 4 distal to the position of cuff 10. Blood flow quality indicator 12 may be used by the operator as a guide to indicate when blood flow transducer 2 has been correctly applied to a digit of the patient's limb and a blood flow signal is obtainable. If the quality of the blood flow signal exceeds predetermined quality criteria as indicated by blood flow quality indicator 12, the operator may then initiate the measurement of LOP by activating LOP key 30 on keypad 26 or LOP key 14 on blood flow transducer 2. Instrument 6 then completes the LOP measurement within 20-40 seconds as described above, by automatically increasing the pressure in cuff 10 to a pressure at which arterial blood flow pulsations can no longer be detected by blood flow transducer 2. Instrument 6 then displays the resulting LOP on display panel 24, together with the RTP, and then deflates cuff 10. For example an LOP of 120 mmHg may be measured with a RTP of 170 mmHg. At this time, physiologic characteristic acquisition module 56 may obtain a patient blood pressure from an external patient monitor or initiate a blood pressure measurement if the results of a recent blood pressure reading were unavailable at the time of the LOP measurement.

The operator then selects a reference pressure level for the pressure of gas to be maintained in cuff 10 during the surgical procedure. The operator may choose to accept the displayed RTP as the reference pressure level or the operator may manually set another reference pressure level based on his or her judgment, experience or the institutional protocol. A Cuff Pressure Safety Margin is then computed based on the measured LOP and selected reference pressure and shown on display panel 34.

For example, an LOP of 120 mmHg is measured, the corresponding RTP of 170 mmHg is displayed, and the operator selects a reference pressure of 180 mmHg for a Cuff Pressure Safety Margin of 60 mmHg. The patient's blood pressure near the time of LOP measurement ($BP_{LOPREF}$) is 90 mmHg.

The subsequent inflation of cuff 10 to a pressure near the selected reference pressure level is then initiated by the operator depressing the "inflate" key on keypad 26. The pressure regulator of instrument 6 then operates to maintain the pressure of gas within cuff 10 near the selected reference pressure level. The reference pressure level may be adjusted and set to a new level at any time by the operator of instrument 6. Physiologic characteristic acquisition module 56 of instrument 6 operated to acquire values of monitored physiologic characteristics throughout the surgical procedure. Controller 32 computes an Updated Cuff Pressure Safety Margin for display and generates alarms if the Updated Cuff Pressure Safety Margin exceeds alarm limits. Referring to the example above, at time during the surgery the patient's blood pressure increases to 130 mmHg due to variations in anesthesia and physiologic response to surgery. An Updated Cuff Pressure Safety Margin of 16 mmHg is computed and displayed $\{SM_U=180-120+1.1(90-130)\}$, the operator is alerted to the change in Safety Margin by an alarm and adjusts the reference pressure to 220 mmHg resulting in an Updated Cuff Pressure Safety Margin of 56 mm Hg.

At the completion of the surgical procedure, the operator initiates the deflation of cuff 10 by activating the deflate key on keypad 26. Cuff 10 is then removed from patient limb 4 immediately after deflation. Cuff 10 may be disconnected from instrument 6 by releasing connectors 18 and 20.

The invention claimed is:

1. A method of determining for a patient an occlusion pressure of a limb to which an inflatable and deflatable cuff is attached to encircle the limb; comprising steps of:
    connecting to the cuff a tourniquet instrument that includes a sensor for sensing a level of pressure in the cuff;
    regulating pressure in the cuff by directing through a port in the cuff a flow of fluid into and out of the cuff;
    detecting an arterial pulsation of blood flow past the cuff and producing a blood flow signal indicative of the blood flow;
    using a controller for responding to the detection of the arterial pulsation by suspending regulation of the pressure in the cuff for a measurement time period; and for
    sensing a level of pressure in the cuff during the measurement time period thereby to provide a cuff pressure signal indicative of the sensed level of pressure in the cuff during the measurement time period; and for
    increasing the cuff pressure level in response to the blood flow signal and cuff pressure signal until blood flow indicated by the blood flow signal decreases to a level less than a minimum detection threshold thereby to produce a limb occlusion pressure value that is a based upon pressure in the cuff sensed during the measurement time period.

2. The method of claim 1 wherein suspending regulation of the pressure in the cuff includes closing valves that control the flow of fluid into and out of the cuff.

3. The method of claim 1 including steps of calculating a recommended tourniquet pressure as the sum of an initial limb occlusion pressure value and a safety margin level and occasionally updating the recommended tourniquet pressure level based upon changes in the patient's physiology.

4. The method of claim 3 including a step of producing an alarm signal when the updated recommended tourniquet pressure level is outside of a predetermined range.

5. The method of claim 1 including steps of attaching a blood flow transducer to a portion of the limb and equipping the transducer with an indicator for producing two signals when a predetermined minimal amount of blood is and is not, respectively, flowing in the portion of the limb.

6. The method of claim 5 including a step of providing the controller in the tourniquet instrument, the method further comprising a step of
    equipping the transducer with a key that is operable to signal the controller to operate.

7. The method of claim 6 including a step of enabling and disabling the operation of the key depending upon the signal produced by the indicator.

8. The method of claim 5 including a step of initializing the blood flow transducer to confirm the transducer is attached to the limb portion.

9. The method of claim 5 including a step of initializing the blood flow transducer to confirm the transducer is unaffected by ambient light above a predetermined threshold level.

10. The method of claim 1 including a step of establishing the measurement time period to be a specific time duration.

11. The method of claim 10 wherein the establishing step includes establishing the measurement time period to be about 30 milliseconds.

* * * * *